United States Patent
Quaka et al.

(10) Patent No.: US 10,085,877 B2
(45) Date of Patent: Oct. 2, 2018

(54) ANTI-SNORING AND SLEEP APNEA DEVICE

(71) Applicants: Gary W. Quaka, Ballwin, MO (US); Darren E. Buddemeyer, Frontenac, MO (US)

(72) Inventors: Gary W. Quaka, Ballwin, MO (US); Darren E. Buddemeyer, Frontenac, MO (US)

(73) Assignee: ORTHO SOLUTIONS, LC, St. Ann, MO (US)

( * ) Notice: Subject to any disclaimer, the term of this patent is extended or adjusted under 35 U.S.C. 154(b) by 276 days.

(21) Appl. No.: 14/120,107

(22) Filed: Apr. 24, 2014

(65) Prior Publication Data

US 2014/0326252 A1 Nov. 6, 2014

Related U.S. Application Data

(60) Provisional application No. 61/854,898, filed on May 3, 2013.

(51) Int. Cl.
*A61F 5/56* (2006.01)

(52) U.S. Cl.
CPC .................. *A61F 5/566* (2013.01)

(58) Field of Classification Search
CPC .... A61C 7/10; A61C 7/36; A61C 9/00; A61C 9/0006; A61F 5/566; A61M 16/0493; A61M 16/0488; A61K 6/10
USPC ..... 433/7, 19, 214, 48, 6; 128/859, 861, 862
See application file for complete search history.

(56) References Cited

U.S. PATENT DOCUMENTS

| | | | |
|---|---|---|---|
| 5,427,117 A | 6/1995 | Thornton | |
| 5,499,633 A | 3/1996 | Fenton | |
| 5,645,422 A | 7/1997 | Williams | |
| 5,769,631 A | 6/1998 | Williams | |
| 5,807,100 A * | 9/1998 | Thornton | A61C 9/00 128/862 |
| 5,919,042 A | 7/1999 | Williams | |
| 5,941,246 A | 8/1999 | Roopchand | |
| 6,036,488 A | 3/2000 | Williams | |
| 6,241,517 B1 | 6/2001 | Williams | |
| 6,247,926 B1 | 6/2001 | Thornton | |
| 6,402,510 B1 | 6/2002 | Williams | |
| 6,464,924 B1 | 10/2002 | Thornton | |
| 6,520,772 B2 | 2/2003 | Williams | |
| 6,719,557 B1 | 4/2004 | Williams | |
| 6,830,051 B1 | 12/2004 | Lesniak et al. | |

(Continued)

*Primary Examiner* — Ophelia A Hawthorne
*Assistant Examiner* — Caitlin Carreiro
(74) *Attorney, Agent, or Firm* — Paul M. Denk

(57) ABSTRACT

An anti-snoring and sleep apnea device has a maxillary tray adapted for receiving upper teeth, the maxillary tray having a pair of shoulder structures with each of the shoulder structures having an adjustable expansion device and a movable boss member connected to the expansion device, with adjustment of each expansion device for moving each boss member away from each shoulder structure, the maxillary tray also having a polymer compound therein, and a mandibular tray adapted for receiving lower teeth, the mandibular tray having a pair of upstanding structural fins, each of the fins being adjacent to each of the boss members, with adjustment of each expansion device for moving the mandibular tray forward of the maxillary tray, the mandibular tray also having a polymer compound therein.

9 Claims, 3 Drawing Sheets

(56) References Cited

U.S. PATENT DOCUMENTS

| | | |
|---|---|---|
| 6,877,982 B2 | 4/2005 | Williams |
| 7,094,051 B2 | 8/2006 | Williams |
| 7,500,851 B2 | 3/2009 | Williams |
| 2008/0149110 A1 | 6/2008 | Baldwin |
| 2008/0149114 A1 | 6/2008 | Baldwin |
| 2010/0263676 A1* | 10/2010 | Thornton ............... A61F 5/566 128/848 |
| 2011/0005526 A1* | 1/2011 | Garabadian ............ A61F 5/566 128/848 |

* cited by examiner

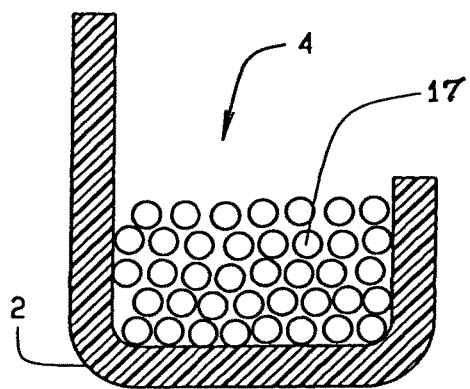
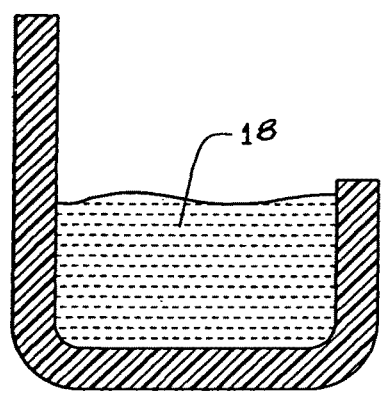
FIG. 6  FIG. 7
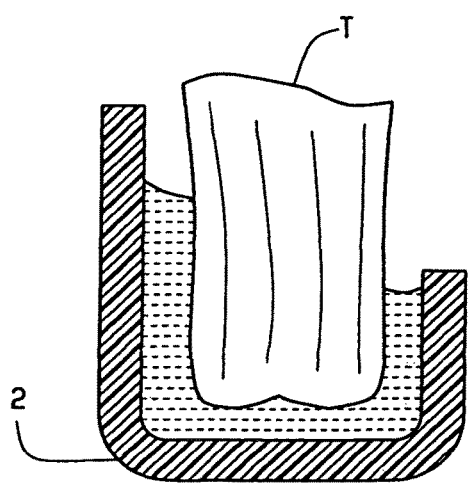
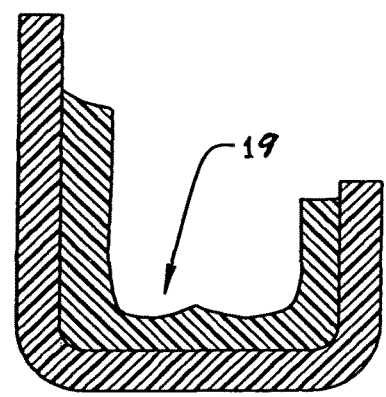
FIG. 8  FIG. 9

ANTI-SNORING AND SLEEP APNEA DEVICE

CROSS REFERENCE TO RELATED APPLICATION

This non-provisional patent application claims priority to the provisional patent application having Ser. No. 61/854,898, filed on May 3, 2013.

FIELD OF THE INVENTION

This disclosure generally relates to an anti-snoring and sleep apnea device that effectively can be adjustably manipulated to add pressure to force the lower jaw of the user to some extent forwardly relative to the upper jaw and thereby attain a sustained greater opening of the air passage, to reduce sleep apnea and related defects.

BACKGROUND OF THE INVENTION

This disclosure generally relates to an anti-snoring and sleep apnea device, with improved structure to allow the device to be adjusted to various conditions that allow for the maximum breathing by the user, during its application.

There are a myriad of teeth, jaw and even various apnea devices that are available in the art. For example, there are many patents on various types of expansion means, Herbst type appliances and related types of structures that are useful for adjusting the alignment, expansion or spread of teeth, or even the movement of one's jaw relative to the other, as when attempting to alleviate an overbite condition. Most of these devices are constructed for the purpose of providing orthodontic benefits to the patient, so as to correct the misalignment of teeth, other structural defects in the arrangement of the teeth and various jaws, relative to each other, so as to furnish a dental correction to either a birth defect, or genetic misalignment of teeth, or to maintain the alignment of teeth after their disruption or breakage as a result of an impact or accident.

Examples of these types of appliances may be seen in the various patents to Williams, such as U.S. Pat. No. 5,645,422, disclosing a mandibular and maxillary arch expander. A similar type of expansion device can be seen in U.S. Pat. No. 5,769,631, on the orthodontic device as invented by Williams. The U.S. Pat. No. 5,919,042, on a mandibular and maxillary arch expander and jaw repositioner, shows the application of the Herbst appliance in providing for movement of the various jaws of the patient relative to each other. A device for providing expansion of the spacing between teeth, on the same jaw level, may be seen in the U.S. Pat. No. 6,036,488, on the pivotal mounting boss for mandibular and maxillary arch expander and jaw repositioner. Other related type patents can be seen in U.S. Pat. Nos. 6,241,517, 6,402,510, 6,520,772, 6,719,557, 6,877,982, 7,094,051 and finally U.S. Pat. No. 7,500,851. As can be noted, all of these devices are for orthodontic purposes; for furnishing the type of improvements to the relationship of teeth and jaws, relative to each other, in order to correct any dental malfunction.

Examples of various types of integrally structured devices for principally holding and sustaining the location of the various jaws of a patient or user, relative to each other, can be seen in a variety of other prior patents. These may be used as protecting devices, or even use for sleep apnea reduction, as can be noted in U.S. Pat. No. 3,217,705, to Roberts, on a mouth piece protector. An apparatus for the prevention of snoring and improved breathing during sleep can be seen in U.S. Pat. No. 5,427,117 to Thornton. Another anti-snoring device can be seen in U.S. Pat. No. 5,499,633 to Fenton. The patent to Roopchand, on an endotracheal tube support, is noted in U.S. Pat. No. 5,941,246, to aid the patient in breathing and during general use for routine anesthesia procedures. The patent to Lesniak, et al, U.S. Pat. No. 6,830,051, shows an interocclusal appliance. The published application to Ballwin, number US 2008/0149110, shows an airway device, including two fixed pillars. Another published application to Ballwin, number US 2008/0149114, shows a similar device. These are examples of structural devices, generally integrally formed, to aid in maintaining the user's air passage opened, for minimizing the effects of sleep apnea. Most of these prior patents, as stated, show the use of integral devices for trying to alleviate sleep apnea, generally without any means for their readjustment, so as to be changeable relative to the user's jaw structure, in order to achieve maximum rearrangement of the jaws, for furnishing the most effective opening of his/her air passage, during usage and application.

Patents that show means for providing for a fixation of the teeth of the jaws of the patient, particularly with respect to application in an oral appliance, for aiding in the realignment of teeth, can be shown in the various patents to Thornton, generally related to dental device having an approved deformable material and method performing same. This can be seen in U.S. Pat. No. 5,807,100 that utilizes aliphatic polyester as a deformable material for application of the user's teeth thereto, when forming the appliance. Such can also be seen in U.S. Pat. No. 6,247,926, disclosing an oral appliance having a bonding layer and methods for fitting and relining the same, during its application and usage. These types of devices are applicable for incorporating the formable material for forming a mold of impressions of some or all of the user's teeth to customize the oral appliance for and to the user's dimensions. The U.S. Pat. No. 6,464,924, to the same inventor, shows a method of forming custom masks using an impression mask and applying the same type of deformable material. These are examples of the known technology to the applicants, primarily relating to orthodontic appliances, mainly for the realignment of teeth, in the first instance and generally integrated structural devices for aiding in the alleviation of sleep apnea, when applied.

The current disclosure provides further and enhanced improvements to this technology, by providing a sleep apnea device that may be adjustable, to the specifics of the user, so as to attain and maintain maximum airway passage, for the user during application of this anti-snoring and sleep apnea device.

SUMMARY OF THE INVENTION

This disclosure contemplates the formation of an anti-snoring and sleep apnea device, one that is not only applicable for using in the mouth of the patient or wearer, in order to alleviate apnea symptoms, but also which may be adjustable, to afford its resetting in order to maximize the expansion of the airway passage for the individual user, in order to substantially reduce sleep apnea on an individual basis. Furthermore, the disclosure contemplates the application of a composition to the mandibular and maxillary trays that hold the teeth in position for both the upper and lower jaw, to assure a precise setting and maintaining of that setting of the appliance within the user's mouth and to fix that setting in its positioning of the jaws, relative to each other, during usage, so that slippage cannot occur, which, may otherwise, affect the expansion of the airway passage, during application of this device.

This anti-snoring and sleep apnea device includes a pair of polymer trays, generally that are custom fitted to provide for the application to the upper maxillary and lower mandible arrangement of teeth in the patient and user. Each one is custom designed to provide for cooperation with each other, to furnish an adjustment in the alignment of these trays, relative to each other, during their application and usage. For example, the lower tray includes an upright structure, generally integrally formed along the outer edge of the mandibular tray, usually having one to each side, normally transversely aligned and which furnishes a surface against which expansion means operatively associated with the maxillary tray can contact. The maxillary tray includes an integrally formed shoulder along its approximate outer back edges, on either side, and which mounts an expansion device or means, such as screws and alignment rods, to provide for adjustment, when installing the device to provide it with its proper setting, for the particular patient involved. The expansion screws connect with a shoulder surface, on each side, and which shoulder devices have a surface generally in alignment with the mandibular tray upright surfaces, so as to provide for their contact, when the expansion screws are adjusted, to provide for a forward movement of the bosses, when forcing the mandibular trays, forwardly, during their adjustment. As previously reviewed, the movement of the lower tray, or mandibular tray, relative to the maxillary tray, forcing a forward shifting of the lower jaw, is what provides for the opening of the patient's air passage, thereby facilitating breathing and generally combating any snoring, or the occurrence of any apnea defects, particularly while the patient sleeps.

To assure that the maxillary tray and mandibular tray remain affixed relative to each other, when the upper and lower teeth of the patient are arranged within their respective trays, a thermal acrylic liner is located within each of the trays and which when subjected to heat, provides for the moldability of such liner, so that when the upper and lower jaw teeth are located within their respective trays, they form an exact impression within the liner material, thus forming a complete and accurate set for the teeth, when the appliance is formed, and keeps the teeth intact within their respective trays, to prevent any slippage between these components, once the liner is formed, impressed and then set, into the precise teeth configuration within their respective liners. Hence, when the device is formed in this manner, all the patient needs to do is to apply the trays to their respective teeth and then adjustment can be made to the expansion device providing for relative shifting forwardly of the bottom tray with respect to the upper tray, until that relatively positioning of the jaws is achieved that furnishes a more clear breathing for the user, in order to reduce the effects of snoring, or apnea, during sleeping.

Generally, the polymeric upper and lower trays forming this device provide the basis for the appliance, through these preferred upper and lower trays, that can be customized for each patient's size and needs. The dorsal fin arrangement, or boss provided on the lower tray is set in alignment with the expansion means and its screws, to help maintain the alignment of the upper and lower trays when positioned within the mouth, and preparing them for repositioning, through adjustment of their screw devices.

The polymer upper and lower trays further include their inner linings, as previously described. This is generally a thermal, acrylic material provided for lining each of the trays of the appliance. This material provides a base for an accurate customization fit of teeth and reduces or eliminates any issues with regard to a tight fitting of the trays on their respective upper and lower sets of teeth. This process eliminates the need for any type of metal retention or even minor adjustment relative to the various components of this device. If any readjustment is needed, the doctor may just reheat the acrylic material, within their trays, in hot water, generally up to approximately 140° F., and then refit the appliance to the patient's mouth, for resetting and adjustment. The expansion module of the device includes its expansion screws. These expansion screws allow for the mandibular tray to be adjusted relative to the maxillary tray, or the upper appliance, to attain that position which allows for a full opening of the air passage of the patient, in order to combat the effects of sleep apnea.

The device of this disclosure comprises an intraoral device that is used for treating snoring and sleep apnea and consists of these two custom fitted polymer trays, which fit over the upper and lower teeth of the patient and engaged by an expansion device, including expansion screws, in order to orient the jaws into a predetermined relationship, that is designed to increase the patient's pharyngeal space, to thereby improve the ability of the patient to exchange air during sleeping.

The acrylic liner that fits within the trays of the device is a thermal responsive type of polymer. The material is capable of being remolded, through thermal action, which means it eliminates the costly remaking of the appliance, after completion of any further dental work on the user. In other words, the liner material may be reheated and repressed against the patient's teeth, in order to furnish a more accurate realignment of the teeth, with respect to the polymer trays. The device is customized for each patient, in accordance with the device and through the usage of its expansion devices, generally screw type of adjustment, enables the mandibular to attain an amount of advancement, generally to be set by the dentist or physician, at the time of its initial fitting, or when readjustment may be required. The prescribing dentist can determine the exact repositioning of the lower bite, or mandibular tray, relative to the wax construction bite obtained from the patient through the operations of the clinician initially forming the device. The dentist may also be able to fine-tune the jaw positioning expansion means, clinically, as needed by altering the screw and/or adjusting the acrylic portions of the appliance, for precise settings.

The functional relationship built into the device acts to position the lower jaw more forwardly of the upper jaw and thereby open vertically from its normal location which causes a slight protrusion of the mandible in relation to the maxilla. This forward repositioning, which is temporary while the appliance is being used, increases the pharyngeal space which assists the patient with improved air exchange, while breathing. Thus, this is the essence of the device; to provide a sleep apnea device that can be fabricated for the particular patient's mouth, having an impression of the patient's exact teeth alignment within the structured trays and then be able to undertake the fine-tuning of the lower jaw repositioning, through the manipulation and adjustment of its expansion device or screws, into a finely constructed personal appliance.

The materials used to fabricate the various components of this device include the upper and lower polymer trays, which may generally, in the preferred embodiment, be made of a methyl methacrylate. Any metal components used in the assembly of the device, such as the expansions screws, are generally made of stainless steel, so as to resist any potential for corrosion. These types of materials have a long history of safe and effective usage, in the manufacture of various dental devices, including the intraoral devices for snoring and obstructive sleep apnea that may be subjected to these types of deterioration.

The upper and lower polymeric trays for the appliance of this disclosure, as previously explained, may be made of methyl methacrylate. These trays may be obtained from a Company by the name of Dentaurum, in Ispringen, Germany.

The polymeric upper and lower tray interlinings, for this device, include a formula of aliphatic polyester, which is a form of self-curing acrylic material. This type of polyester may include a polycaprolactone polymer that may be subject to heat treatment and formation of the indentation of the patient's teeth, to provide for a precise seat for the teeth after the material has cooled and hardened, in preparation for usage within the device. This material is generally sold under the trademark Thermacrylic and is available from Airway Management, Inc., located in Dallas, Tex. The material is a dimensionally stable polymer, yet hardens to a tough, unbreakable plastic and may be remolded when subjected to heat, as previously explained, is non-toxic and may even soften in water. It is sold under Model Number 06-OBVS-12.

The expansion modules, namely, the expansion screws that are used in conjunction with the particularly formed trays for the applicant's device, are stainless steel screws that are also available from said Dentaurum Company.

Generally, the anti-snoring and sleep apnea device of this disclosure is intended to reduce night time snoring and mild to moderate obstructive sleep apnea, principally in adults. The devices are worn while sleeping, to support the lower jaw in a more forwardly position, as may be prescribed by the dentist or doctor specializing in throat disorders. Obviously, the device can be readily applied by the patient and removed, as desired.

Therefore, the present disclosure provides an anti-snoring and sleep apnea device that is effective for principally shifting the lower jaw of the patient more forwardly, to open and sustain the opening of the user's air passage, particularly while sleeping.

The present disclosure provides a device for the treatment of snoring and sleep apnea, to improve the health of the user.

The present disclosure is directed to a sleep apnea device that incorporates upper and lower trays, for cooperating with the teeth of the maxillary and mandibular, in order to provide for that precise adjustment and fitting of the device when worn by the user.

Still further, a sleep apnea device is disclosed wherein its upper and lower trays may include a moldable polymeric acrylic, that can be applied, in the softened state, against the teeth of the user, in order to furnish a precise impression for fixing the teeth to their respective upper and lower trays, to assure the precise and maintenance of the setting of the device when worn.

The present disclosure also provides upper and lower trays for a sleep apnea device, that are applied to the teeth and which incorporate a biasing device, which may be adjusted to furnish a resetting in the miniscule to more advanced forward movement to the mandibular or lower jaw, of the patient, during wearing of this device.

The present disclosure also provides a sleep apnea device that can be applied by the user and removed, or even reapplied nightly, for application in minimizing snoring and reducing sleep apnea.

The present disclosure is further directed to a sleep apnea device including maxillary and mandibular trays, for cooperating with teeth and which may be readjusted in the teeth impressions within their inner liners, particularly after dental work may have been performed on the patient subsequent to the original construction and setting of the said device.

These and other advantages may become more apparent to those skilled in the art upon review of the disclosure as provided herein and upon undertaking a study of the description of its preferred embodiment, in view of the drawings.

BRIEF DESCRIPTION OF THE DRAWINGS

In referring to the drawings,

FIG. 6 shows the same view of the upper tray as shown in FIG. 5, with the deposition of the polymeric acrylic heat sensitive material applied therein, in preparation for its heating and molding into the impression of the user's teeth;

FIG. 7 shows the same view of FIG. 6, with the polymeric acrylic having been heated, into a molded consistency, in preparation for application for a teeth impression;

FIG. 8 provides the same view of FIG. 7 and shows the location of a tooth within the upper tray during the molding of its polymeric acrylic to a tooth impression;

FIG. 9 shows the tooth impression of the hardened inner liner after the tooth has been removed from therein;

DESCRIPTION OF THE PREFERRED EMBODIMENT

Figure 1:
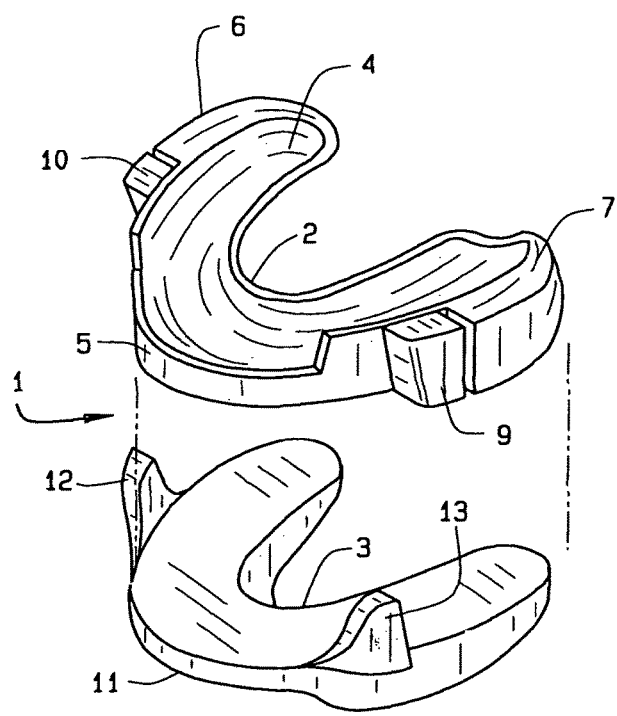
FIG. 1 provides an isometric view of the upper and lower trays for the anti-snoring and sleep apnea device constructed according to the present disclosure.
Figure 2:
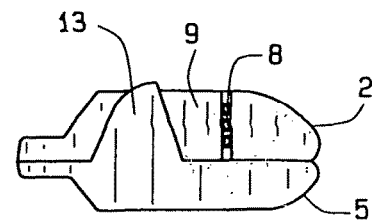
FIG. 2 is a side view of the upper and lower trays, of FIG. 1, before any expansion adjustment has been made.
Figure 3:
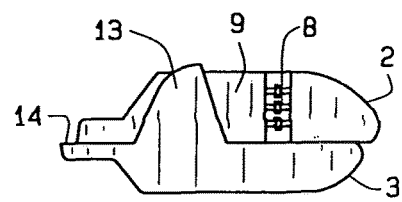
FIG. 3 shows a side view of the device of FIG. 2, after the expansion screw has been adjusted to provide for relative forward movement of the bottom tray with respect to its compatible upper tray.

In referring to the drawings and in particular FIG. 1, therein is shown the anti-snoring and sleep apnea device or appliance 1 of this disclosure. It includes an upper tray structure 2 and lower tray structure 3, both of which are of arcuate configuration and designed to provide an opened surface or trough, as can be seen at 4, with respect to the upper tray 2, for locating of the maxillary teeth therein. The same type of opening is provided on the bottom of the lower or mandibular tray 3, as can be understood.

As can be noted, the upper tray 2 includes an integral arcuate structure that extends entirely around its perimeter, as can be seen at 5 and has a broadened integral structure or shoulders, as at 6 and 7, formed at their rearward ends, as seen. These shoulders 6 and 7 mount the expansion screws, as can be seen at 8 in FIGS. 2-5, for cooperating with their respective boss members 9 and 10, which when the expansion screws 8 and associated expansion screw mechanisms are manipulated and adjusted, provide for the forward advancing of said members 9 and 10, for purposes to be herein described. These expansion screws 8 can be obtained from the commercial source as previously described in the Summary. The expansion screws 8 are fixed permanently with the shoulders 6 and 7.

The bottom or mandibular tray 3 also includes an arcuately configured tray member 11, which provides its downwardly disposed tray for accommodating the bottom teeth of the user therein, as can be understood. The arcuate member 11 includes a pair of upstanding mounts structures, or fins, as at 12 and 13 and these mounts 12 and 13 are disposed for being matingly contacted by the boss members 9 and 10, as can generally be seen in FIGS. 2 and 3. Thus, when the appliance 1 is in place and the maxillary portion of the user's jaw locates within tray 2, and the mandibular set of teeth of the user locate within the downwardly disposed trough of tray 3, the upper and lower trays, as at 2 and 3, are generally in alignment with each other, such that when the expansion screws 8 are adjusted, in a manner as known in the trade, it forces the boss members 9 and 10 forwardly, against the aligned surface of the upright structures 12 and 13, as can be readily seen within these figures. Thus, when the expansion screws 8 are expanded, it forces the bottom tray 3 to be advanced somewhat forwardly relative to the tray 2, generally as noted by the displacement shown at 14, such that the lower jaw advances at least to that dimension and does have a tendency to further open the air passage of the user, with a tendency to reduce the effects of snoring or apnea, particularly while sleeping.

Figure 4:
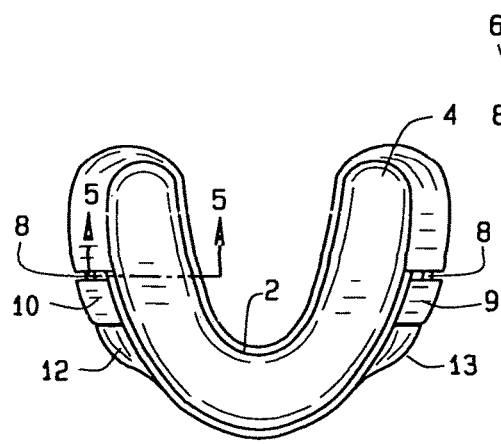
FIG. 4 is a top plan view of the mated upper and lower trays of the device when assembled for usage.

FIG. 4 shows how upper tray 2 conveniently mates with the lower tray 3, such that the boss members 9 and 10 shift or move in association with their screws 8. The boss members 9 and 10 are aligned over the bottom tray 3, as can be seen from the positioning of the upright structures, or the fins 12 and 13, for the said mandibular tray 3.

Figure 5:
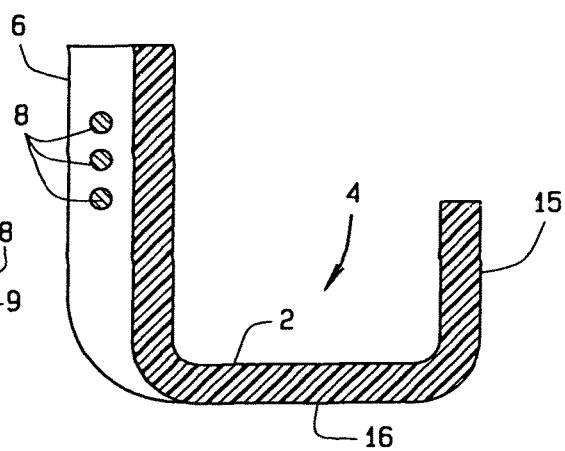
FIG. 5 provides a sectional view of the upper tray taken along the line 5-5 of FIG. 4.

FIG. 5 provides a cross-sectional view of the upper or maxillary tray 2, with its broadened structure 6, or the exterior side of the tray 2 and a narrower wall 15 on the interior side, all being integrally formed with a base 16 of the shown tray 2. Thus, as can be seen, the expansion screws 8 are embedded and affixed, within the shoulder 6 and extend forwardly, for mounting of their associated expansion screw mechanisms therein. A similar type structure for open surface 4 of the maxillary member 2 is provided as a mirror image on the opposite side, as can be understood. Furthermore, the bottom tray 3 has a related configuration such as the open surface 4, the exterior side of the tray and a narrower wall 15 on the interior side, but without the broadened shoulder feature, as also can be seen in FIG. 1.

FIG. 6 shows the initial stage of preparation of the teeth impression aspects of the upper tray 2 and the lower tray 3, for use for sleep apnea purposes. It is noted, in this instance, the cavity or open space 4 of the upper maxillary tray 2 has the application of a quantity of the thermal acrylic liner pellets and composition applied therein, as can be noted at 17. The same procedure is followed with respect to the cavity of the lower or mandibular tray 3. Then, when heat is applied to the acrylic liner laden or filled tray 2, it has a tendency to soften, into a configuration that can be molded, generally as noted at 18, in FIG. 7. The composition of the acrylic liner has already been summarized and discussed above in this application. Following its heating, the maxillary tray 2 is applied to the upper teeth, the mandibular tray 3 is applied to the lower teeth, and FIG. 8 shows a somewhat cross-sectional view showing the application of a tooth T of the patient, into the upper tray 2, to form an impression in the soften acrylic liner of the entire set of upper teeth around the arcuate tray 2 of the device 1.

FIG. 9 shows a somewhat cross-sectional view with the teeth T removed, showing the precise impression of the teeth, as noted at 19, within their respective trays 2 or 3. Thus, when the impression has been made and the acrylic liner has cooled, both the maxillary tray 2 and mandibular tray 3 will have a precise impression of the teeth of the prospective user, to provide for a very fixed setting and application of the device 1, to the upper and lower set of teeth of the patient, in preparation for usage and expansion of its expansion screws 8, to provide for a forced opening of the air passage, as previously reviewed.

Figure 10:
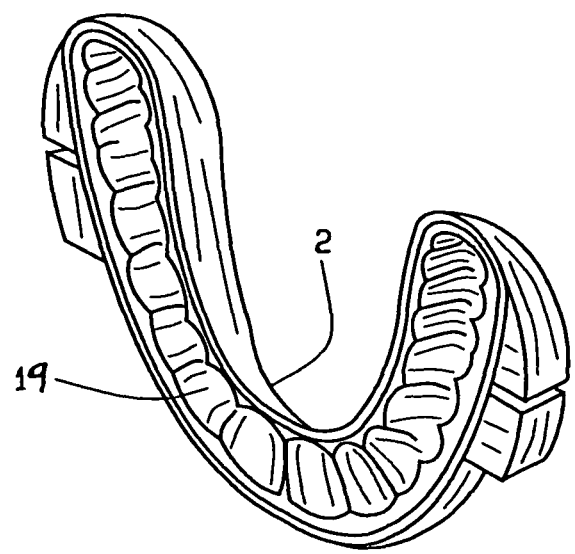
FIG. 10 shows the complete maxillary tray with the teeth alignment molded therein, in preparation for usage of the anti-snoring and sleep apnea device.
Figure 11:
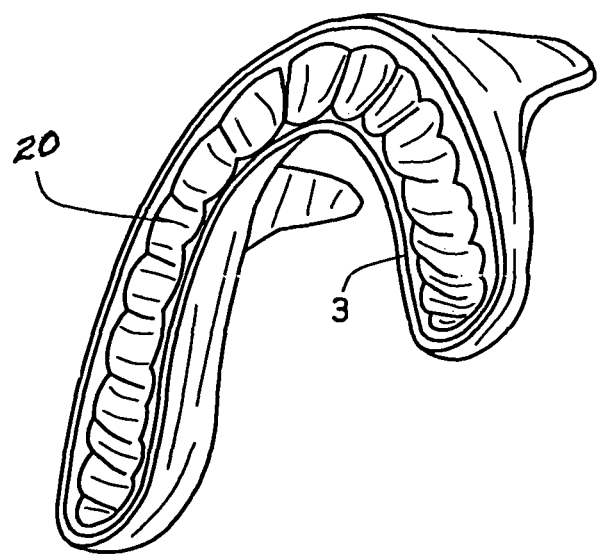
FIG. 11 shows the bottom or mandibular tray having a complete teeth alignment molded within its inner liner in preparation for its application as an anti-snoring and sleep apnea device.

FIG. 10 shows the maxillary tray 2 with its teeth impressions 19, entirely around its arcuate configuration, while FIG. 11 shows the impressions 20 formed of the mandibular tray 3, as previously reviewed.

The thermal acrylic liner, once fixed, will provide a very close connection and contact with the set of teeth, throughout the patient's usage of this apnea device 1. But, should the patient have any dental work done on his/her teeth, all one need do is to simply heat, as aforesaid, the various trays 2 and 3, until the acrylic liners become softened and reapply the trays 2 and 3 to the user's teeth, for a re-impression of the teeth with respect to the liners of the trays 2 and 3 for future usage and application.

A brief review of the procedure for providing an accurate fit of the maxillary tray 2 and mandibular tray 3 to the patient can generally be described as follows. First of all, the device 1 is fabricated with a thermal acrylic liner. The precise fit of the teeth within the liners is ideal for any patient who may require future dental work, such as restorations, crown or bridgework, since the acrylic material is remolded numerous times and therefore eliminates the costly remakes of any device after completion of further dental work. In some situations, the doctor, orthodontist, dentist, or technician, may not feel comfortable with how the thermal acrylic liner has formed about the teeth. Hence, the thermal liner can be revised, by just following the reheating and realigning procedures outlined herein. To achieve such, the appliance 1 is simply placed in a hot water bath at 160° until the thermal liner turns clear. If too much heat is applied, the appliance may warp, which may make it inefficient. Once the material becomes clear, the trays 2 and 3 should be quickly removed from the hot water and then allowed to cool for approximately thirty seconds. Following this, the trays 2 and 3 are fitted as an appliance onto the patient's arch, or teeth. The maxillary tray 2 will be applied to the upper set of teeth, while the mandibular tray 3 will be applied to the lower set of teeth. Once the impression is made, after approximately one minute, the appliance 1 may be removed from the patient's teeth. Once the appliance 1 is removed, any excess thermal material may be trimmed away, with the available dental appliances used for such purposes. The appliance 1 is then allowed to cool until the thermal material turns white. Any burrs may be burnished to remove rough edges, until smooth. Then, the appliance 1 should conveniently fit securely on all of the teeth of the patient, when applied for usage. Adjustment of the expansion screws 8 will normally be done by the doctor, unless the patient is clearly instructed how to perform such personally.

The foregoing provides what is believed to be a thorough description of the concept of this anti-snoring and sleep apnea device 1. Obviously, other types of polymer or acrylic liners that may be harden, generally by heat, could be used as the liner material for forming the teeth impressions.

Variations or modifications to the subject matter of this disclosure may occur to those skilled in the art upon review of the disclosure as provided herein. Such variations or modifications, if within the spirit of this disclosure, are intended to be encompassed within the scope of any claims to patent protection issuing hereon. The description of the preferred embodiment, the depiction of the device in the drawings and other explanatory materials, is generally set forth for illustrative purposes only.

We claim:

1. An anti-snoring and sleep apnea device comprising:
a maxillary tray adapted for receiving upper teeth, the maxillary tray being of arcuate design, with rearward ends, and said maxillary tray having a pair of broadened integral structures at their rearward ends extending laterally outward from the arcuate design of the maxillary tray and forming shoulder structures thereat, each of the shoulder structures having a front facing face, an adjustable expansion device comprising expansion screws mounting at one end to the front facing face of the shoulder structure with the expansion device extending forwardly from said front facing face, and a movable boss member connected to the ends of the expansion screws of the adjustable expansion device with each movable boss member having a front surface, forwardly of said front facing face of the shoulder structure, and with adjustment of each of the expansion screws of the adjustable expansion device providing for moving of each boss member forwardly and away from the front facing face of each shoulder structure of said device; and
a mandibular tray adapted for receiving lower teeth, said mandibular tray having an arcuate design, with rearward ends, and said mandibular tray having a pair of upstanding structural fins, each having an aligned surface, said structural fins also being arranged laterally outwardly of the mandibular tray, and each of the structural fins being forwardly adjacent to each front surface of said boss members and arranged in contact therewith, with the adjustment of each expansion device for moving the mandibular tray forwardly of the maxillary tray through pressure biasing of each of the front surfaces of the boss members against a respective aligned surface of the upstanding structural fins of the mandibular tray, with adjustment of each expansion device for moving under pressure the mandibular tray forwardly of the maxillary tray, thereby relieving sleep apnea during application of said device.

2. The anti-snoring and sleep apnea device of claim 1 including both said maxillary tray and said mandibular tray having a polymer compound therein for making a precise impression of the teeth of the user to provide a fixed setting and application of the device with the maxillary and mandibular teeth of the user.

3. The anti-snoring and sleep apnea device of claim 1 wherein the expansion screws are stainless steel.

4. The anti-snoring and sleep apnea device of claim 1 wherein the expansion devices each comprise three expansion screws connected to each of the shoulder structures.

5. The anti-snoring and sleep apnea device of claim 2 wherein the polymer compound comprises methyl methacrylate.

6. The anti-snoring and sleep apnea device of claim 2 wherein the polymer compound comprises aliphatic polyester.

7. The anti-snoring and sleep apnea device of claim 2 wherein the polymer compound comprises a self-curing acrylic material.

8. The anti-snoring and sleep apnea device of claim 2 wherein the polymer compound comprises polycaprolactone polymer.

9. The anti-snoring and sleep apnea device of claim 2 wherein the polymer compound may be heated and reheated.

* * * * *